United States Patent [19]
Okazaki et al.

[11] Patent Number: 4,652,544
[45] Date of Patent: Mar. 24, 1987

[54] SOLID ACID CATALYST OF ACID-TREATED HYDRATED NIOBIUM OXIDE AND METHOD FOR ITS PREPARATION

[75] Inventors: Susumu Okazaki, Ibaragi; Tokio Iizuka, Hokkaido; Satoshi Kado, Kanagawa, all of Japan

[73] Assignee: CBMM Internacional Ltda., Sao Paolo, Brazil

[21] Appl. No.: 767,982

[22] Filed: Aug. 21, 1985

[30] Foreign Application Priority Data

Aug. 21, 1984 [JP] Japan ................. 59-173974

[51] Int. Cl.[4] .............................................. B01J 27/14
[52] U.S. Cl. .................................................... 502/208
[58] Field of Search .......................... 502/208; 568/898

[56] References Cited

U.S. PATENT DOCUMENTS

| | | | |
|---|---|---|---|
| 2,055,269 | 9/1936 | VanPeski et al. | 568/898 |
| 2,162,913 | 6/1939 | Eversole et al. | 568/898 |
| 2,691,647 | 10/1954 | Field et al. | 502/208 X |
| 3,014,899 | 12/1961 | Engel | 502/208 X |
| 3,342,847 | 9/1967 | Kruse | 502/208 X |
| 3,582,184 | 12/1974 | Siskin et al. | 502/208 X |
| 4,193,807 | 3/1980 | Ishibashi et al. | 501/901 X |

OTHER PUBLICATIONS

Chemical Abstracts, 97:227,7384, p. 796, Thermal Field Stability . . . , Palatnik et al.
Chemical Abstracts, 84:185,614d, p. 362, Complexing of Niobium (V) . . . , Gorelov et al.
Chemical Abstracts, 94:204,722N, p. 246, Metallic Acids . . . , Rao.
Chemical Abstracts, 99:46924b, p. 551, Intercolation into Niobium Oxide Phosphate . . . , Bereke et al.

Primary Examiner—Andrew H. Metz
Assistant Examiner—William G. Wright
Attorney, Agent, or Firm—Beveridge, DeGrandi & Weilacher

[57] ABSTRACT

A solid state catalyst consists essentially of hydrated niobium oxide containing a phosphoric acid on its surface in an amount sufficient to increase surface acidity, to inhibit crystallization of the niobium oxide and to retard loss in catalytic activity following exposure to high temperature. The catalyst can be prepared by treating hydrated niobium oxide ($Nb_2O_5 \cdot xH_2O$) or an anhydride thereof with a phosphoric acid. The catalyst is useful in the hydration of ethylene to form ethanol.

12 Claims, 5 Drawing Figures

SOLID ACID CATALYST OF ACID-TREATED HYDRATED NIOBIUM OXIDE AND METHOD FOR ITS PREPARATION

BACKGROUND OF THE INVENTION

This invention relates to a solid acid catalyst consisting essentially of acid-treated hydrated niobium oxide (or acid-treated niobic acid) a method for preparing the catalyst and the use of the catalyst in the hydration of olefins, such as ethylene.

Several procedures using sulphuric acid or aluminum chloride as catalysts are known in the chemical industry. There are many problems associated with the use of these catalysts. Among the problems are separation and recovery of the catalysts, treatment of water from the catalytic processes, corrosion of equipment and installations, formation of by-products, coloration of products, and so forth. In the case of aluminum chloride, there is also the problem of consumption of large quantities of the catalyst. It has been proposed to substitute mineral acids, such as sulphuric acid, phosphoric acid and the like, for solid acid catalysts.

There is practically no catalyst consisting of a solid acid suitable for use in the presence of water, except for certain ion exchange resins. These resins, however, have not been found to be entirely satisfactory because of their price, tendency to disaggregate and their limited range of application.

More recently, fluoride resin products, such as Nafion Type H, have been proposed. While these resins have a higher acidity than ion exchange resins, the acidity is still not sufficient and the resins are characterized by an extremely high price.

Hydrated niobium oxide (niobic acid) has been proposed as a solid acid catalyst. The niobium oxide catalyst can be prepared from hydrated niobium oxide (niobic acid) by washing the oxide with water followed by thermal treatment at low temperature. The hydrated niobium oxide can also be treated with sulphuric acid or hydrofluoric acid followed by a thermal treatment at low temperature, thus obtaining a niobium oxide catalyst which is a solid acid.

Even the niobium oxide catalysts have not proved entirely satisfactory. Crystallization occurs in these catalysts at high temperatures, such as a temperature at 400° C., and mainly over a temperature of 500° C. Crystallization in the catalyst results in deterioration of catalytic activity, thus prohibiting the use of these catalysts in reactions carried out at such high temperatures.

Niobium oxide catalysts that have lost some of their catalytic activity can be reactivated by heating the catalyst at an elevated temperature. If reactivation must take place at a temperature exceeding 400° C., it is apparent that such a temperature could hardly be attained in practical terms to reactivate the catalyst, and this fact makes the utilization of hydrated niobium oxide catalysts difficult on an industrial scale.

Accordingly, there exists a need in the art for a solid acid catalyst that does not substantially crystallize at high temperature, does not exhibit a decrease of catalytic activity after exposure to high temperature, has improved surface acidity and is not poisoned by water.

SUMMARY OF THE INVENTION

Accordingly, this invention aids in fulfilling these needs in the art. The invention is the result of arduous research made on a catalyst formed by hydrated niobium oxide, which is a solid acid. Niobic acid is treated according to the invention with phosphoric acid to give the resulting acid-treated hydrated niobium oxide catalyst a high surface acidity and to simultaneously inhibit the crystallization of the catalyst; crystallization decreases catalytic activity.

More particularly, the present invention provides a solid acid catalyst consisting essentially of hydrated niobium oxide containing a phosphoric acid on its surface in an amount sufficient to increase surface acidity of the niobium oxide, to inhibit crystallization of the niobium oxide following exposure to high temperature and to retard loss in catalytic activity following exposure to high temperature.

This invention also provides a method for preparing the solid acid catalyst of the invention. The method comprises treating hydrated niobium oxide or an anhydride thereof with a phosphoric acid in an amount and under conditions sufficient to increase surface acidity of the niobium oxide, to inhibit crystallization of the niobium oxide following exposure to high temperature and to retard loss in catalytic activity following exposure to high temperature.

The acid-treated niobic acid of this invention can be used for hydration of ethylene, alkylation, etc., and chemical reactions that can be accelerated by an acid catalyst.

This invention provides a process for preparing alcohol by hydration of an olefin. The process comprises reacting the olefin with water in the presence of a catalytically effective amount of the solid acid catalyst of the invention.

BRIEF DESCRIPTION OF THE DRAWINGS

This invention will be more fully understood by reference to the following detailed description and the accompanying drawings in which.

DETAILED DESCRIPTION

Figure 1:
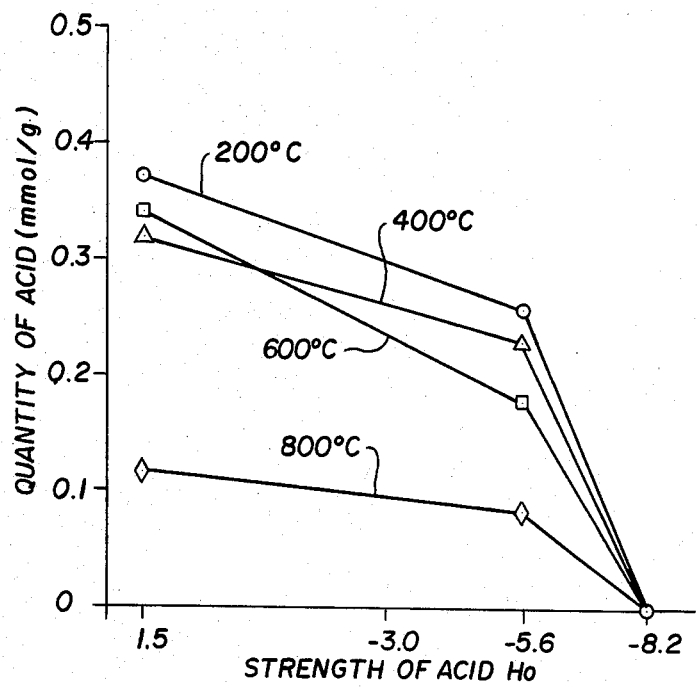
FIG. 1 is a diagram showing the relationship between the strength of surface acidity of hydrated niobium oxide at different temperatures treated with a solution containing 0.5 moles per liter phosphoric acid.
Figure 2:
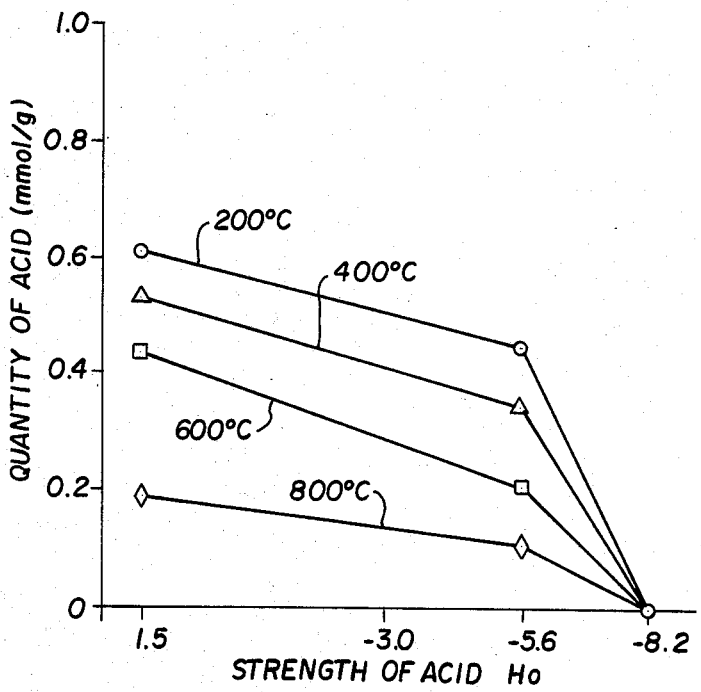
FIG. 2 is a diagram showing the strength of surface acidity of a hydrated niobium oxide at various temperatures treated with a solution containing 1.0 mole per liter phosphoric acid as a function of the amount of acid.

The present inventors treated hydrated niobium oxide, i.e. niobic acid ($Nb_2O_5 \cdot xH_2O$), with a 0.5 mole per liter phosphoric acid solution and a 1.0 mole per liter phosphoric acid solution. The treated niobic acid was subjected to thermal treatment at temperatures of 200° C., 400° C., 600° C. and 800° C., successively. A treated niobic acid with a relatively high surface acidity of $H_o \leq -5.6$ was obtained. The results of this work are shown in FIGS. 1 and 2. It has been found that the amount of surface acidity maintained at a high temperature exceeding 600° C. is practically independent of the concentration of the phosphoric acid.

Figure 3:
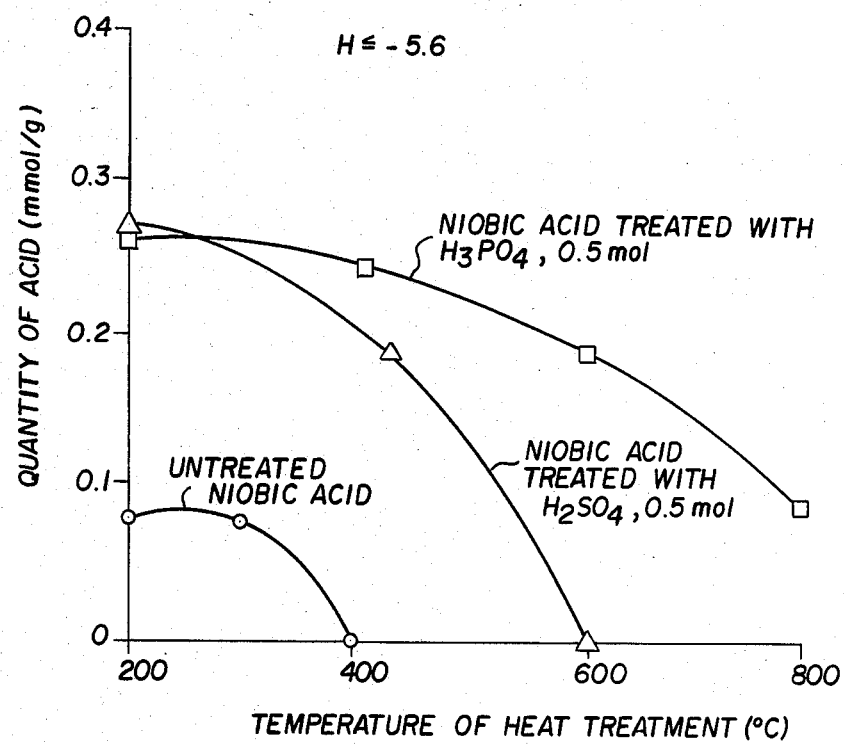
FIG. 3 is a diagram showing the relationship between temperature and the amount of acidity at $H_o \leq -5.6$ of treated niobic acids.

Referring to FIG. 3, niobic acid treated with phosphoric acid according to the invention is compared with untreated niobic acid and niobic acid treated with sulphuric acid. The Figure shows that the niobic acid treated with phosphoric acid according to the invention exhibits stable, high surface acidity even when heated at a temperature exceeding 500° C., and even up to 800° C.

It is theorized that these phenomena are due to the condensation of phosphoric acid on the niobic acid forming non-volatile, polyphosphoric acid on the niobic acid surface. It is also theorized that the amount of phosphoric acid inhibits the crystallization of the niobic acid at high temperature while producing at the same time the high surface acidity. Furthermore, the fact that the niobic acid can be treated with a relatively dilute 0.5 mole per liter phosphoric acid solution demonstrates that the ability to maintain strong acidity at high temperature does not depend on the concentration of the phosphoric acid used for the treatment. The phosphoric acid forms a polyphosphoric acid film or something like that capable of covering the niobic acid.

It has also been found that the catalyst of the invention is resistant to poisoning by water; acidity can be maintained in the presence of water. Thus, the catalyst of the invention is a solid acid that shows good catalytic activity, especially in the hydration of olefins and other acid catalyzed reactions carried out in the presence of water, such as hydration, esterification, Beckmann rearrangement reactions and the like. An example demonstrating the catalytic activity of the catalyst of the invention in the hydration of ethylene follows.

Figure 4:
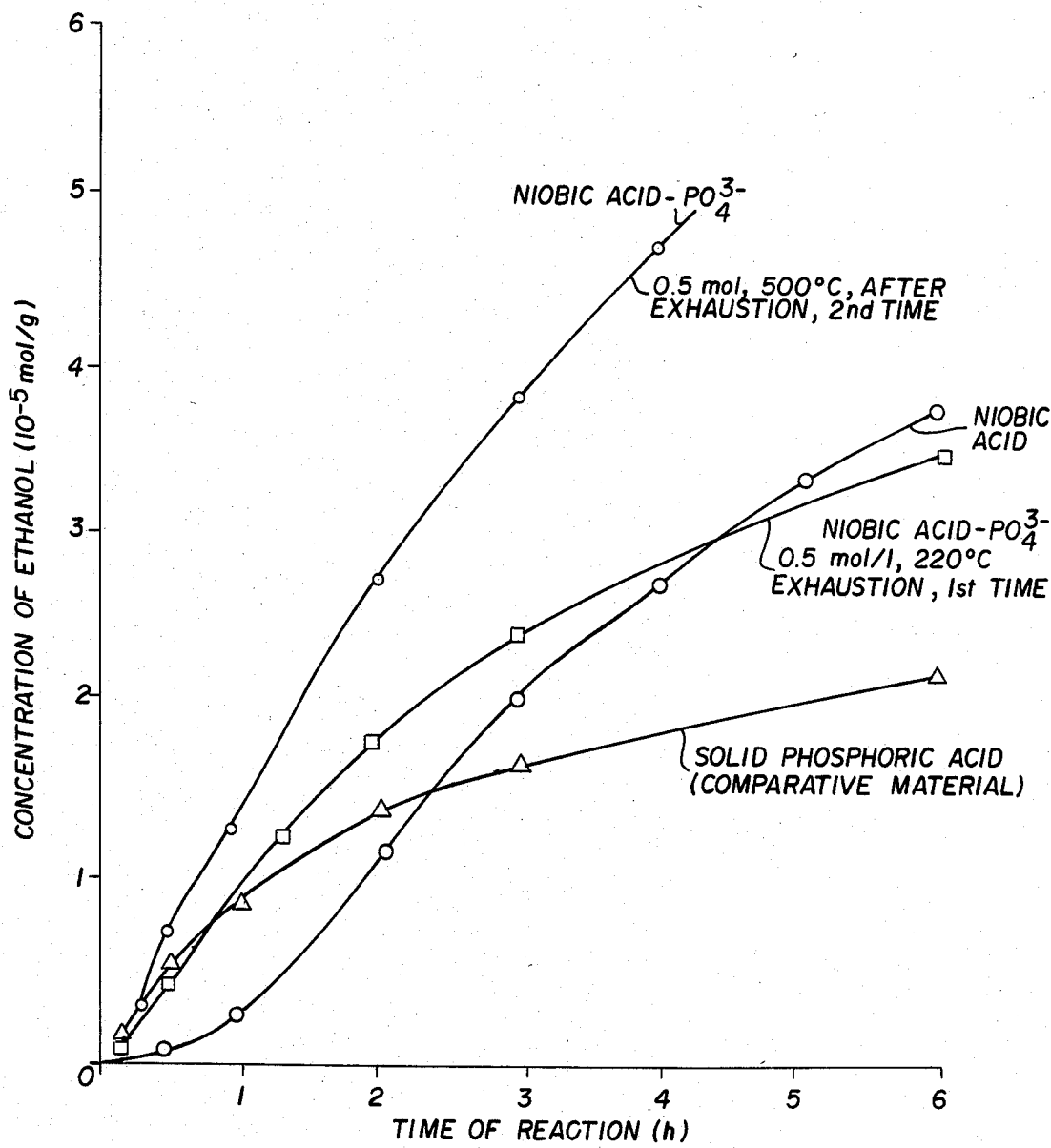
FIG. 4 shows the catalytic activity of hydrated niobium oxide treated with phosphoric acid (0.5 mol/l) according to the invention for ethylene hydration.
Figure 5:
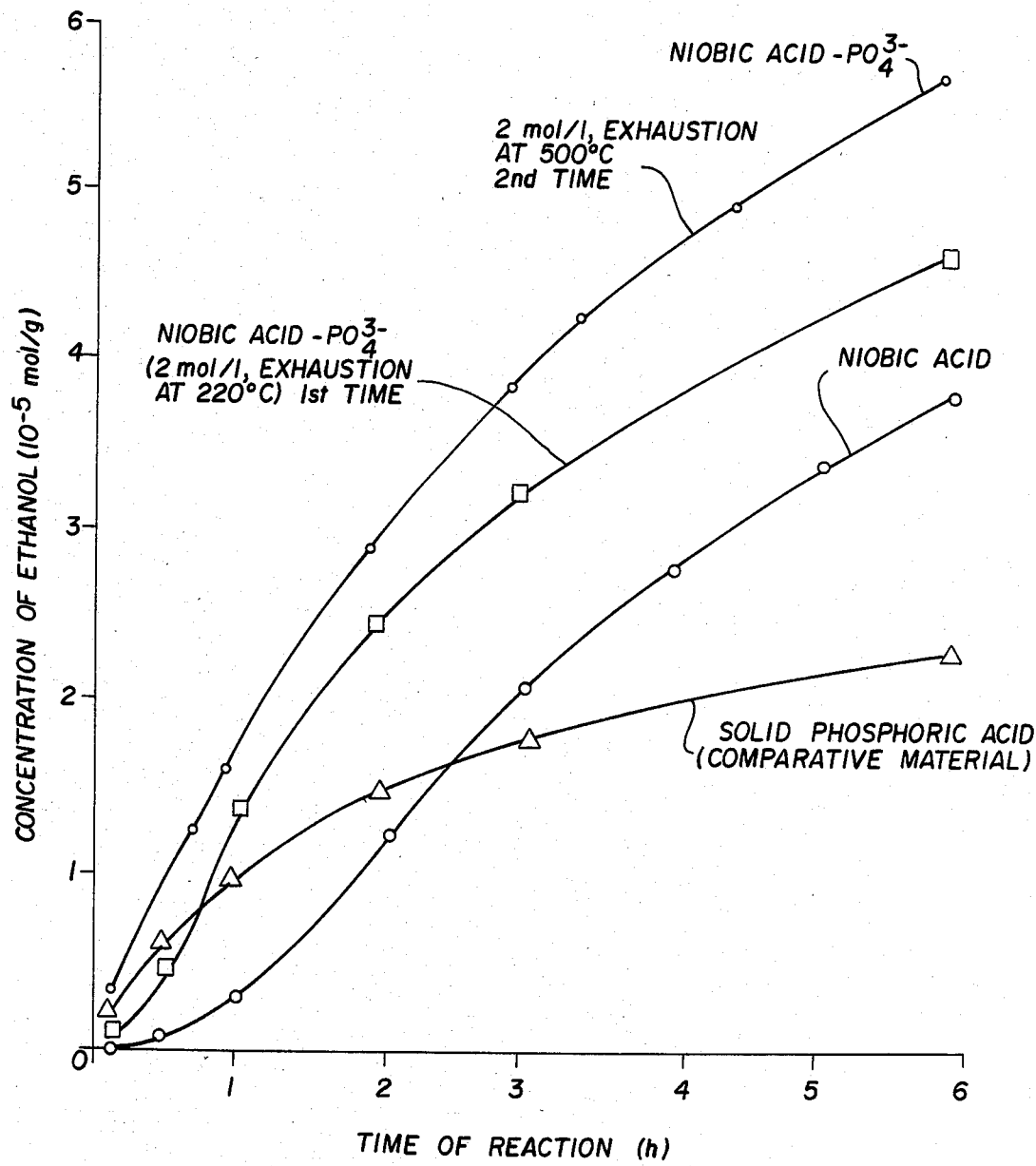
FIG. 5 shows the catalytic activity of niobic acid treated with phosphoric acid (2 mol/l) for ethylene hydration.

FIGS. 4 and 5 show the catalytic activity of niobic acid treated with 0.5 mole per liter and 2 moles per liter phosphoric acid solutions in the hydration of ethylene to form ethanol. The reactions were carried out in equipment suitable for gas phase reaction in a circulating system. The Figures show the corresponding catalytic activity of untreated niobic acid and of solid phosphoric acid under the same reaction conditions.

As clearly shown in the Figures, the untreated niobic acid exhibits a higher catalytic activity than that of the solid phosphoric acid. Nevertheless, at the beginning of the reaction, the catalytic activity was quite low, thus demonstrating the existence of an induction period. In contrast, niobic acid treated with phosphoric acid according to the invention shows high catalytic activity right from the beginning of the reaction. Special attention should be given to the fact that, when the reaction is restarted after the catalyst is degassed by heating at a high temperature of 500° C., the catalytic activity increases even more. In contrast, the catalytic activity of the untreated niobic acid remains markedly lower even after degassing of the catalyst at a temperature of 300° to 400° C.

Calculation of the specific surface can be made using test procedures involving X-ray diffraction of a pulverized sample, mass differential thermal analysis, nitrogen absorption and similar methods. The results show that rapid crystallization occurs in untreated niobic acid at a temperature close to 550° C. When niobic acid is treated with phosphoric acid according to the invention, only a trace of crystallization shows up even if the temperature is elevated to 600° C.

The following data was obtained to determine the influence on catalytic activity of the concentration of phosphoric acid used for treating the niobic acid.

In the first reaction, niobic acid was treated with 2 moles per liter of phosphoric acid. As shown in FIG. 5, the resulting catalyst had a higher activity than niobic acid treated with only 0.5 mole per liter phosphoric acid as shown in FIG. 4.

The catalyst was heated and degassed at 500° C. In the second reaction, the catalytic activity of treated niobic acid was a constant value independent of concentration of the phosphoric acid. It is theorized that this is due to the level of strength of surface acidity of the niobic acid, which is $H_o \leq -5.6$, after treatment at high temperature as shown in FIGS. 1 and 2. On the other hand, while the catalytic activity is markedly superior to that of solid phosphoric acid, the effect of treating niobic acid with phosphoric acid is not merely due to the amount of phosphoric acid that condenses and becomes associated with the niobic acid. The catalytic activity is also due to the fact that the phosphoric acid is fixed to the niobic acid surface and becomes spread out and widely distributed.

This invention will be more fully understood by reference to the following Example.

EXAMPLE 1

Niobic acid ($Nb_2O_5 \cdot xH_2O$) in an amount of 10 grams was immersed in 30 ml of aqueous phosphoric acid ($H_3PO_4$) solution, 0.5 or 1.0 mole per liter, and aged for 48 hours. The mixture was dried in ambient air at 120° C. After hardening, the material was ground to form grains passing a 100 mesh screen. The grains were collected and used as a catalyst in the hydration of ethylene to form ethanol.

Each catalyst thus prepared was heated by a hot air flux for 2 hours at an established temperature inside a tubular reactor and subsequently used for the ethylene hydration reaction. The reactor used for the experiment was an air-tight installation of 200 ml capacity equipped with a circulation system. Hydration equipment was installed immediately after the discharge from the tubular reactor. Water (5 ml) was placed in the equipment and immersed in a tank maintained at a constant temperature. Steam was fed to the hydration equipment at constant pressure. In order to prevent the condensation of water, the entire reaction system was maintained at a prescribed temperature by a coil heater.

The product formed was dissolved in the hydration equipment, and a sample was removed and analyzed by gas chromatography. The reaction conditions were as follows:

| Amount of catalyst | 0.8 to 0.9 g |
|---|---|
| Ethylene partial pressure | 400 Torr |
| Steam partial pressure | 55 Torr |
| Reaction temperature | 220° C. |

For purposes of comparison, the reaction was carried out with untreated niobium oxide, niobium oxide treated with sulphuric acid at 0.1 mole per liter, niobium oxide treated with hydrofluoric acid (1.3 weight percent), solid phosphoric acid, hydrated niobium oxide treated with phosphoric acid (2 moles per liter) and hydrated niobium oxide treated with phosphoric acid (0.5 mole per liter). The results are summarized in Table I.

TABLE I

HYDRATION OF ETHYLENE

| Catalyst | Number of days for reaction | Temperature of exhaustion flux (°C.) | Rate of Formation of Ethanol ($g^{-1}h^{-1}$) | Maximum Acid Strength |
|---|---|---|---|---|
| $Nb_2O_5$ | 1 | 220 | 0.83 | −8.2 |
| $Nb_2O_5$—$SO_4{}^{2-}$ (treated with $H_2SO_4$ - 0.1 mol/l) | 1 | 220 | 1.33 | −8.2 |
| $Nb_2O_5$—$F^-$ (treated with HF 1.3% by weight) | 1 | 220 | 1.11 | −8.2 |
| Polyphosphoric Acid | 1 | 220* | 0.70 | |
| $Nb_2O_5$—$PO_4{}^{3-}$ (treated with $H_3PO_4$ - 2 mol/l) | 1 | 220 | 1.31 | |
| $Nb_2O_5$—$PO_4{}^{3-}$ (treated with $H_3PO_4$ - 2 mol/l) | 2 | 500 | 1.53 | |
| $Nb_2O_5$—$PO_4{}^{3-}$ (treated with $H_3PO_4$ - 0.5 mol/l) | 1 | 220 | 0.99 | |
| $Nb_2O_5$—$PO_4{}^{3-}$ (treated with $H_3PO_4$ - 0.5 mol/l) | 2 | 500 | 1.55 | |

*After reaching 220° C., the time of exhaustion of flux was 3 minutes. The remaining time was 2 hours.

Reaction involving the use of untreated niobic acid was carried out for 3 hours at 200° C., and when the catalyst was used again an increase in catalytic activity was observed. However, when the catalyst was used at a temperature exceeding 400° C., the catalytic activity rapidly decreased to 0.

When the catalyst was treated with sulphuric acid or hydrofluoric acid, an increase in catalytic activity resulted. However, the catalytic activity disappeared when the reaction was carried out at high temperature and when the catalyst was used at a high temperature.

Solid phosphoric acid is currently in use for hydrating ethylene on an industrial scale. High catalytic activity was observed under the above-mentioned conditions at the beginning of the reaction. However, catalytic activity was greatly reduced after 2 hours exhaustion. It is theorized that this was due to evaporation of a portion of the phosphoric acid during the reaction.

When the niobic acid catalyst treated with phosphoric acid according to the invention is compared with the untreated niobic acid or niobic acid treated with other acids, high catalytic activity was observed from the beginning of the reaction. When the catalyst of the invention was reactivated by degassing at high temperature, its catalytic activity became even higher.

In summary, this invention provides a solid catalyst possessing high acidity. The catalyst consists essentially of hydrated niobium oxide prepared by treating the niobium oxide or its anhydride with phosphoric acid to increase the surface acidity of the oxide, inhibit crystallization of the niobium oxide and retard the loss in catalytic activity following exposure of the catalyst to high temperature. The catalyst is useful in accelerating reactions involving the hydration of olefins, such as ethylene, alkylation by alcohols, and other reactions that are accelerated by the presence of an acid. The catalyst of the invention does not crystallize even at high temperatures, such as temperatures over 500° C. Furthermore, catalytic activity does not degenerate at high temperatures. Therefore, it is possible to employ the catalyst of the invention in high temperature reactions. Furthermore, it is possible to reactivate the catalyst of the invention by heating it at temperatures over 400° C. In addition, the catalyst of the invention is not poisoned by water. The catalyst has a wide range of applications in industrial processes.

What is claimed is:

1. A solid acid catalyst consisting essentially of hydrated niobium oxide containing a phosphoric acid on its surface in an amount sufficient to increase surface acidity of said niobium oxide, to inhibit crystallization of said niobium oxide following exposure to high temperature and to retard loss in catalytic activity following exposure to high temperature.

2. Solid acid catalyst according to claim 1 wherein the catalyst has a surface acidity $H_o \leq -5.6$.

3. Solid acid catalyst according to claim 1 wherein said catalyst contains condensed phosphoric acid on its surface.

4. Solid acid catalyst according to claim 3 wherein said condensed phosphoric acid is non-volatile polyphosphoric acid.

5. Solid acid catalyst according to claim 1 which is in the form of finely divided grains.

6. Solid acid catalyst according to claim 3 wherein said phosphoric acid is widely distributed on the catalyst surface.

7. Solid acid catalyst according to claim 3 wherein said phosphoric acid is evenly distributed on the catalyst surface.

8. Solid acid catalyst according to claim 2 wherein said catalyst is resistant to poisoning by water.

9. A method for preparing a solid acid catalyst as claimed in claim 1 comprising treating hydrated niobium oxide or an anhydride thereof with a phosphoric acid in an amount and under conditions sufficient to increase surface acidity of said niobium oxide, to inhibit crystallization of said niobium oxide following exposure to high temperature and to retard loss in catalytic activity following exposure to high temperature.

10. Method according to claim 9 wherein said niobium oxide is treated with a 0.5 to 2.0 mol/liter solution of phosphoric acid.

11. Method according to claim 10 comprising treating said niobium oxide by immersion in orthophosphoric acid and aging the resulting mixture without agitation.

12. Method according to claim 11 comprising removing treated niobium oxide from said mixture and heating the treated niobium oxide in air at an elevated temperature to dry the treated niobium oxide.

* * * * *